United States Patent [19]

Colle et al.

[11] Patent Number: 4,529,437
[45] Date of Patent: Jul. 16, 1985

[54] HERBICIDES

[75] Inventors: Roberto Colle, Milan; Franco Gozzo, S. Donato Milanese; Ciro Preziuso, Milan, all of Italy; Antony G. M. Barrett; Derek H. R. Barton, both of London, United Kingdom

[73] Assignee: Montedison S.p.A., Milan, Italy

[21] Appl. No.: 159,517

[22] Filed: Jun. 16, 1980

[30] Foreign Application Priority Data

Jun. 15, 1979 [IT] Italy ................................ 23622 A/79

[51] Int. Cl.$^3$ .................... A01N 43/40; A01N 43/84; A01N 47/30
[52] U.S. Cl. ............................................ 71/94; 71/88; 71/99; 544/160; 546/244; 564/17; 564/48
[58] Field of Search ....................... 71/99, 120, 94, 88; 564/17, 48; 544/160; 546/244

[56] References Cited

U.S. PATENT DOCUMENTS

| | | | |
|---|---|---|---|
| 3,008,989 | 11/1961 | Boehne et al. | 564/17 X |
| 3,146,262 | 8/1964 | Schafer et al. | 71/99 X |
| 3,759,991 | 9/1973 | Marks | 71/99 X |
| 3,903,084 | 9/1975 | Ducharme | 564/48 X |

OTHER PUBLICATIONS

Held et al., Zeitschrift der Chemie, vol. 13, (1973), p. 341.
Srivastrava et al., J. Ind. Chem. Soc., vol. 40, (1963), p. 803.

Primary Examiner—Catherine L. Mills
Attorney, Agent, or Firm—Stevens, Davis, Miller Mosher

[57] ABSTRACT

Thiocarbamoyl-guanidine derivatives having herbicide activity are disclosed.

The process for their preparation and their use as herbicides are disclosed too.

1 Claim, No Drawings

HERBICIDES

THE PRIOR ART

Only a limited number of compounds belonging to the class of thiocarbamyl-guanidines, are known from technical literature.

Held, Gross and Schibert [Zeitschrift der Chemie 13, 341 (1973)], by oxidation of the N,N-dimethyl-N'-phenyl-thiourea with thionyl chloride, prepared $N^1,N^1$-dimethyl-$N^2,N^3$ diphenyl-$N^3$-[N,N-dimethyl-thiocarbamoyl]-guanidine of the formula:

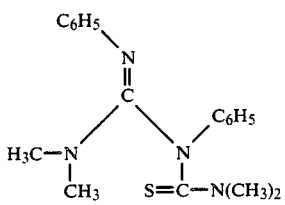

Srivastrava and co-workers [J. Ind. Chem. Soc. 40, 803 (1963)] prepared derivatives of thiocarbamoyl-guanidine non substituted on the nitrogen atom in position 1 and on the nitrogen atom of the thiocarbamoyl group, in the form of bromohydrates.

To the class of thiocarbamoyl-guanidine derivatives, however, herbicide activity has never been previously recognized.

THE PRESENT INVENTION

We have now found, and this forms an object of this invention, that the compounds of the general formula:

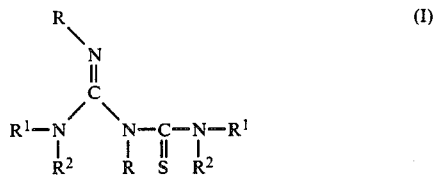

wherein:

R = phenyl, optionally substituted by one or more halogen atoms or alkyl groups with from 1 to 3 carbon atoms optionally, in their turn, halo-substituted;

$R^1$ and $R^2$ (equal to or different from each other) = alkyl or O-alkyl groups with from 1 to 3 carbon atoms, or $R^1$ and $R^2$ together form an alkylidenic chain having 4 or 5 carbon atoms optionally interrupted by a hetero-atom, are endowed with a high herbicide activity and can be used in a method for fighting infesting weeds.

All compounds of Formula I, except those in which $R^1 = = R^2 =$ methyl when R = unsubstituted phenyl, are new compounds and form a further object of this invention.

The preparation of the compounds of General Formula I, and this constitutes another object of this invention, is achieved by reacting a formamidine sulfide or disulfide (II)

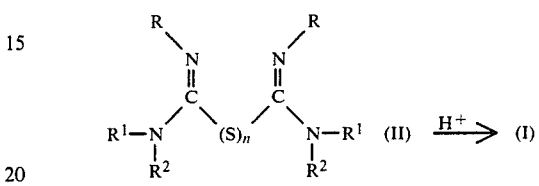

(wherein R, $R^1$ and $R^2$ have the same meanings indicated in General Formula I and wherein n = either 1 or 2), with a catalytic amount of a strong anhydrous acid.

The compounds of General Formula II have been described in the co-pending Italian Patent Application No. 23,621 A/79.

The above cited reaction is preferably carried ut by adding a catalytic amount of an acid having a sufficient force to salify the basic groups of the sulphide or disulphide of Formula II, to a solution of this latter in an aprotic polar solvent such as for instance chloroform ($CHCl_3$). An anhydrous halogenhydric acid or a trihaloacetic acid maybe used as a strong acid.

The reaction rate depends, on the nature of the formula II compound that is made to react and also on the amount of acid used.

For amounts of acid of about 0.1 equivalents per mol of compound of formula II, at room temperature the reaction is complete within a few minutes.

Once the reaction has taken place, the chloroformic solution is washed with a saturated aqueous solution of sodium bicarbonate ($NaHCO_3$) and is then anhydrified. The solvent is then evaporated under vacuum, thereby obtaining as a residue the corresponding compound of formula I which may thereupon be purified by crystallization.

Compounds reported on the following Table 1 have been prepared according to the above described method.

TABLE I

Compounds of formula:

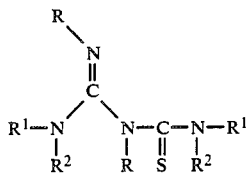

| COMPOUND n° | R | $R^1$ | $R^2$ | Elemental Analysis theor. (%) | found (%) | $NMR^{(1)}$ (δ, ppm) | $M.P.^{(2)}$ (°C.) | $IR^{(3)}$ ($cm^{-1}$) | Rough Formula M.W. |
|---|---|---|---|---|---|---|---|---|---|
| 1 | 3,4-$Cl_2$—$C_6H_5$ | $CH_3$ | $CH_3$ | C 46.57 H 3.68 N 12.08 | 46.08 3.76 11.81 | | 125–127 | | $C_{18}H_{18}N_4SCl_4$ 463.8 |
| 2 | $C_6H_5$ | $CH_3$ | $CH_3$ | C 66.2 | 66.55 | 7.53– | 119–120 | 1625, | $C_{18}H_{22}N_4S$ |

TABLE I-continued

Compounds of formula:

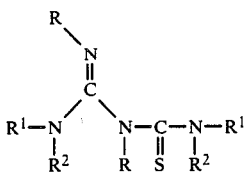

| COMPOUND n° | R | R¹ | R² | Elemental Analysis theor. (%) | found (%) | NMR[1] (δ, ppm) | M.P.[2] (°C.) | IR[3] (cm⁻¹) | Rough Formula M.W. |
|---|---|---|---|---|---|---|---|---|---|
|  |  |  |  | H 6.9<br>N 17.15 | 6.85<br>17.2 | 6.61(10Hm)<br>2.9 (6H,s)<br>2.53 (6H,s) |  | 1580,<br>1300<br>1080<br>765,<br>695 | 326.47 |
| 3 | 4-$CH_3$—$C_6H_4$ | —$CH_2$—$CH_2$—O—$CH_2$—$CH_2$— | | C 65.72<br>H 6.89<br>N 12.74 | 65.2<br>6.95<br>13.01 | | 142–145 | | $C_{24}H_{30}N_4SO_2$<br>438.59 |
| 4 | 4-$CH_3$—$C_6H_4$ | —$CH_2$—$(CH_2)_3$—$CH_2$— | | C 71.85<br>H 7.88<br>N 12.89 | 68.98<br>7.68<br>12.82 | | 193–197 | | $C_{26}H_{34}N_4S$<br>434.65 |
| 5 | 4-$CH_3$—$C_6H_4$ | $CH_3$ | $CH_3$ | C 67.75<br>H 7.39<br>N 15.8 | 66.99<br>7.33<br>16.1 | | 170,5–<br>172,5° C. | | $C_{20}H_{26}N_4S$<br>354.52 |
| 6 | 4-Cl—$C_6H_4$ | $CH_3$ | $CH_3$ | C 54.68<br>H 5.1<br>N 14.17 | 54.46<br>4.97<br>14.22 | | 161–163 | | $C_{18}H_{20}N_4SCl_2$<br>396.36 |
| 7 | 4-Cl—$C_6H_4$ | —$CH_2$—$(CH_2)_3$—$CH_2$— | | C 60.62<br>H 5.93<br>N 11.78 | 60.62<br>5.99<br>11.83 | | 186–189 | | $C_{24}H_{28}N_4SCl_2$<br>475.49 |
| 8 | 4-Cl—$C_6H_4$ | —$CH_2$—$CH_2$—O—$CH_2$—$CH_2$— | | C 55.12<br>H 5.04<br>N 11.69 | 55.29<br>4.86<br>11.22 | | 189–194 | | $C_{22}H_{24}N_4SO_2Cl_2$<br>479.41 |
| 9 | 3-$CF_3$—$C_6H_4$ | —$CH_2$—$CH_2$—O—$CH_2$—$CH_2$— | | N 10.25<br>F 20.86 | 9.86<br>20.66 | | 174–175 | | 546.52 |
| 10 | 3-$CF_3$—$C_6H_4$ | $CH_3$ | $CH_3$ | S 6.93 | 6.72 | | oil | | 462.45 |
| 11 | 3-$CF_3$—$C_6H_4$ | —$CH_2$(—$CH_2)_3$—$CH_2$— | | S 5.91 | 5.59 | | 142–146 | | 542.58 |
| 12 | 3,4-$Cl_2$—$C_6H_3$ | —$CH_2$—$CH_2$—O—$CH_2$—$CH_2$— | | C 48.19<br>H 4.04<br>N 10.21 | 47.29<br>3.96<br>9.99 | | 153–155 | | $C_{22}H_{22}N_4O_2Cl_4$<br>548.32 |
| 13 | 3,4-$Cl_2$—$C_6H_3$ | —$CH_2$—$(CH_2)_3$—$CH_2$— | | C 52.95<br>M 4.81<br>N 10.29 | 52.08<br>4.75<br>10.08 | | 156–160 | | $C_{24}H_{26}N_4SCl$<br>544.38 |

NOTES to Table 1:
[1]NMR = spectrum of nuclear magnetic resonance. The spectra have been recorded using $CDCl_3$ as solvent and TMS as internal standard. s = singlet. m = multiplet
[2]The melting point has not been corrected.
[3]IR = Infrared spectrum.

Only the more significant bands are reported on the table.

The compounds of general formula I are endowed with a high herbicide activity exerted against monocotiledones as well as against dicotiledones.

The activity data of some of the representative compounds, obtained as described in example 2, have been reported on the following Table 2.

The herbicide activity has been tested on the following infesting weeds:

MONOCOTILEDONES

A = *Echinocloa crusgalli*
B = *Avena fatua*
C = *Lolium italicum*
D = *Sorghum spp.*
E = *Setaria glauca*
F = *Digitaria sanguinalis*
G = *Alopercurus myosuroides*
H = *Panicum dichotomiflorum*
I = *Festuca pratense*
J = *Bromus sterilis*
K = *Poa annua.*

DICOTILEDONES

L = *Setllaria media*
M = *Ipomea purpurea*
N = *Vigna sinensis*
O = *Rumex acetosella*
P = *Galinsoga parviflora*
Q = *Convolvolus sepium*
R = *Convolvulus ariensis*
S = *Geranium dissect*
T = *Sida spinosa*
U = *Brassica*
V = *Gypsophila muralis.*

The herbicide activity data reported on Table 2 have been expressed on the basis of a scale of values ranging from 0 (no herbicidal activity, growth of the plant equal to that of the check) to 4 (death of the plant or complete stopping of the growth).

TABLE 2

| COMPOUND N° (see Table 1) | Treatment | Dose Kg/ha | Monocotyledones | | | | | | | | | | | Dicotyledones | | | | | | | | | | |
|---|---|---|---|---|---|---|---|---|---|---|---|---|---|---|---|---|---|---|---|---|---|---|---|
| | | | A | B | C | D | E | F | G | H | I | J | K | L | M | N | O | P | Q | R | S | T | U | V |
| 1 | Pre-emergence | 6 | 2 | | | | | 4 | | 4 | 4 | | 4 | 4 | | | 4 | 4 | | | | | 4 | |
| | Post-emergence | 6 | 4 | 4 | 4 | 4 | 4 | 4 | 4 | 4 | 4 | 4 | | 4 | 4 | 4 | 4 | | 4 | 4 | 4 | 4 | 4 | |
| 10 | Pre-emergence | 6 | | | | | | | | | | | | 4 | 3 | 3 | | | | | | | | |
| | Post-emergence | 2 | 4 | | | | 4 | | | 3 | | | | 4 | 4 | 4 | 4 | | 4 | 4 | 4 | | | 4 |

Depending on the particular compound the best effectiveness of the herbicide activity is achieved by application in pre-emergence or in post-emergence, that is when the infesting weeds have not yet emerged out of the soil or when they have. The herbicide compounds of the invention prove also to be selective with respect to useful cultivations such as wheat, maize, soja and cotton.

For agricultural applications, the active compounds are distributed on the soil as such or, preferably, in form of suitable compositions consisting of one or more of the compounds of formula I as the active principle and one or more suitable carriers. Suitable compositions include wettable powders, liquid pastes, granular formulates, and so on. Suitable carriers include, depending on the type of composition, silica, caolin, diatomaceous earths, bentonite, pomix, organic solvents or water.

In these compositions, additives such as surfactants, emulsifiers, thickeners, and so on may also be included. A list of carriers and additives is reported in "Mc Cutcheons—Detergent and Emulsifiers—North American and International Editions, 1977 Annual. Mc Cutcheons Publ. Co., Glen Rock, N.J. (U.S.A.)".

The preparation of said compositions is carried out according to procedures common to the formulation practice.

If desired, other active ingredients such as fertilizers, insecticides or fungicides may also be included in these compositions.

The amount of active principle (Compounds of formula I) to be distributed on the soil depends on various factors such as the environmental conditions, the kind of agricultural cultivation to be protected from infesting weeds, the type of composition, and the particular active principle. Generally, amounts of compounds of formula I comprised between 1 and 6 Kg/ha are suitable for obtaining good results in the fight against infesting weeds, the preferred amount being of about 2–3 Kg/ha.

To better illustrate the present invention, the following examples will now be given.

EXAMPLE NO. 1

Preparation of $N^1,N^1$-dimethyl-$N^2,N^3$-diphenyl-$N^3$-[(N,N-dimethyl)-thiocarbamoyl]guanidine (Compound No. 2 on Table 1)

43 μl of trifluoroacetic acid were added to a solution of $N^1,N^1$-dimethyl-$N^2$-phenyl-formamidine-disulphide (2 g, 5.58 $10^{-3}$ mols) in chloroform (200 ml).

The reaction mixture was then allowed to rest for 15 minutes at room temperature, after which it was washed with a saturated solution of $NaHCO_3$, and anhydrified with anhydrous $Na_2SO_4$. After removal of the solvent by evaporation under vacuum, the residue was crystallized by n.hexane/benzene (70:30). 1.3 grams of the desired pure product were obtained (with a 71% yield). The other compounds recorded on Table 1 have been prepared by analogous procedures.

EXAMPLE NO. 2

Determination of the herbicide activity

Pots were prepared having a diameter of 10 cm and height of 10 cm containing sandy soil and one of the infestants listed at pages 7 and 8 was then sown into each pot. Water, in the amount required for a good sprouting of the seeds, was then added into each pot. The pots were subdivided into three sets. The first set of pots was not treated with any kind of herbicide and was used as a check series.

The second set was treated, one day after sowing, with a hydroacetonic dispersion (20% volume/volume) of the compounds of the invention, to evaluate the herbicide activity in pre-emergence.

The third series was treated 15 days after the sowing (that is, when the plants, depending on the species, already had a height of 5–10 cm) with a hydroacetonic dispersion (20% volume/volume) of the compounds of the invention in order to evaluate the herbicide activity in post-emergence.

All the pots were kept under observation in an environment conditioned at a temperature between 15° and 24° C., with a relative humidity of 70%, a photoperiod of 12 hours, and with a light intensity of 2500 lux.

Every two days the pots were uniformly sprinkled so as to ensure a degree of humidity sufficient for a good development of the plants. After 28 days from the treatment, controls of the vegetative stage of the plants were carried out and the evaluation has been expressed on the basis of a value scale ranging from 0 (growth equal to that of the check) to 4 (complete stopping of growth or total destruction of the plant).

What we claim is:

1. A method for fighting infestations of monocotyledons and dicotyledons both in pre-emergence or in post-emergence, characterized in that on the soil there is spread, either as such or in a suitable composition, an effective amount of at least one herbicidal compound having the formula:

$$\begin{array}{c} R \\ \diagdown \\ N \\ \| \\ C \\ \diagup \diagdown \\ R^1-N \quad N-C-N-R^1 \\ | \quad\quad | \; \| \; | \\ R^2 \quad R \; S \; R^2 \end{array} \qquad (I)$$

wherein:
R = phenyl optionally substituted by one or more halogen atoms or alkyl groups with from 1 to 3 carbon atoms optionally in their turn halo-substituted;

$R^1$ and $R^2$ (equal to or different from each other) = alkyl or O-alkyl groups with from 1 to 3 carbon atoms, or $R^1$ and $R^2$, together with the nitrogen atom to which they are bonded, form a piperidino or a morpholino group.

* * * * *